United States Patent [19]
Burnham

[11] Patent Number: 5,792,401
[45] Date of Patent: Aug. 11, 1998

[54] METHOD FOR MAKING A TUBULAR PRODUCT

[76] Inventor: Warren R. Burnham, Drawer 312, Glens Falls, N.Y. 12801

[21] Appl. No.: 653,886

[22] Filed: May 28, 1996

Related U.S. Application Data

[63] Continuation of Ser. No. 474,729, Mar. 22, 1990, abandoned, which is a continuation-in-part of Ser. No. 845,492, Mar. 31, 1986, Pat. No. 4,764,324, which is a continuation of Ser. No. 743,890, Jun. 13, 1985, abandoned, which is a continuation of Ser. No. 560,526, Dec. 12, 1983, abandoned.

[51] Int. Cl.$^6$ .................................................. B29C 47/02
[52] U.S. Cl. ............................... 264/103; 264/171.29
[58] Field of Search ........................ 64/103, 171.29; 428/36.3; 138/126, 132; 604/280

[56] References Cited

U.S. PATENT DOCUMENTS

| | | | |
|---|---|---|---|
| 2,989,778 | 6/1961 | Frenkel | 425/114 |
| 3,249,666 | 5/1966 | French | 264/103 |
| 3,558,754 | 1/1971 | Martin | 264/173 |
| 3,585,707 | 6/1971 | Stevens | 264/173 |
| 3,961,873 | 6/1976 | Brown | 425/114 |
| 4,135,869 | 1/1979 | Loyer | 264/173 |
| 4,219,522 | 8/1980 | Oyama | 264/173 |
| 4,321,226 | 3/1982 | Markling | 264/173 |
| 4,764,324 | 8/1988 | Burnham | 264/173 |

FOREIGN PATENT DOCUMENTS

| | | | |
|---|---|---|---|
| 899206 | 7/1984 | Belgium . | |
| 102422 | 3/1984 | European Pat. Off. | 264/173 |
| 2613782 | 10/1977 | Germany . | |
| 1349843 | 4/1974 | United Kingdom | 264/173 |
| 1584616 | 2/1981 | United Kingdom | 264/173 |
| 8304182 | 12/1983 | WIPO . | |

*Primary Examiner*—Leo B. Tentoni
*Attorney, Agent, or Firm*—Ronald P. Kananen

[57] ABSTRACT

A process for making a reinforced tubular product, especially a catheter, in a single extrusion step. A reinforcing member is applied to an extruded thermoplastic catheter body of about its finished size which is softened by heating while tensioning the reinforcing member to control the surface deformation or penetration of the catheter wall by the reinforcing member to produce an irregular surface contour on the catheter body. The catheter body is then smoothed in a sizing die burying the reinforcement to form the finished product. The heating step may be in addition to or substituted by a curing step when a thermosetting or cross-linking material is used for the body. The reinforcement may be braid, or a helical wrap of one or more members applied at one or more controlled angles relative to the axis of the catheter to control the apparent stiffness and torque transmission efficiency of the catheter. The process is particularly adapted to making a catheter having its reinforcement interrupted to provide a unitary non-reinforced distal tip. By this process, the radial location of the reinforcement in the wall of the catheter is easily controlled according to the material of the body, the heating conditions, and the tension on the reinforcing member. Multiple extrusions to form a reinforced catheter body are thus not required.

15 Claims, 7 Drawing Sheets

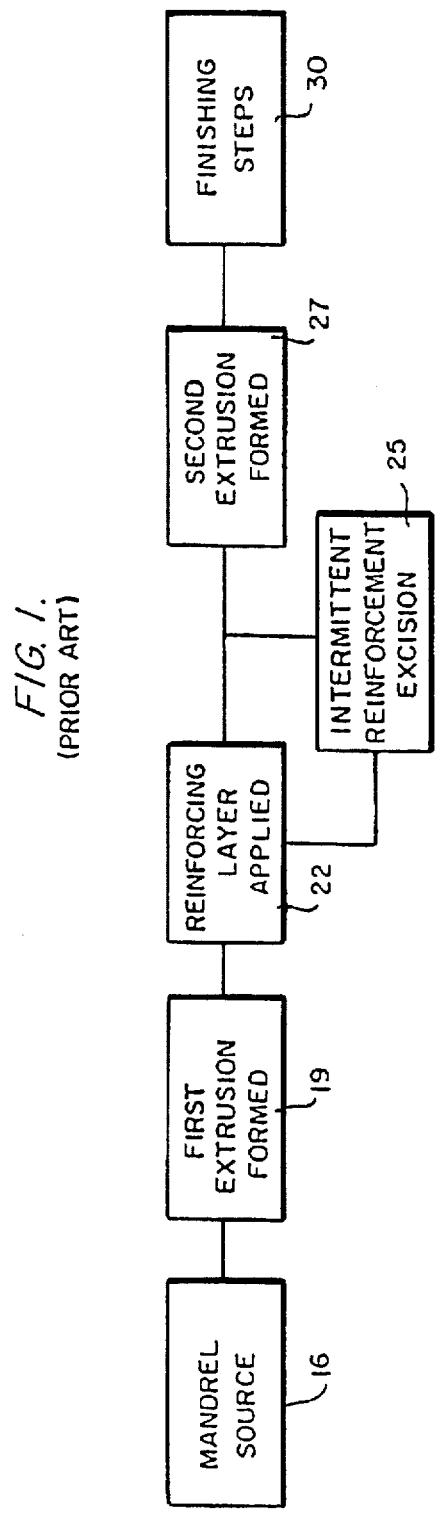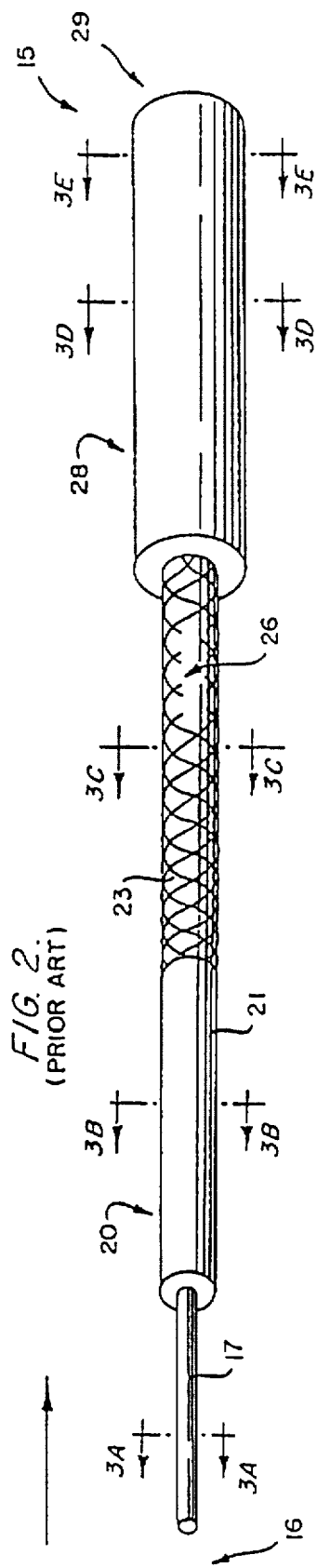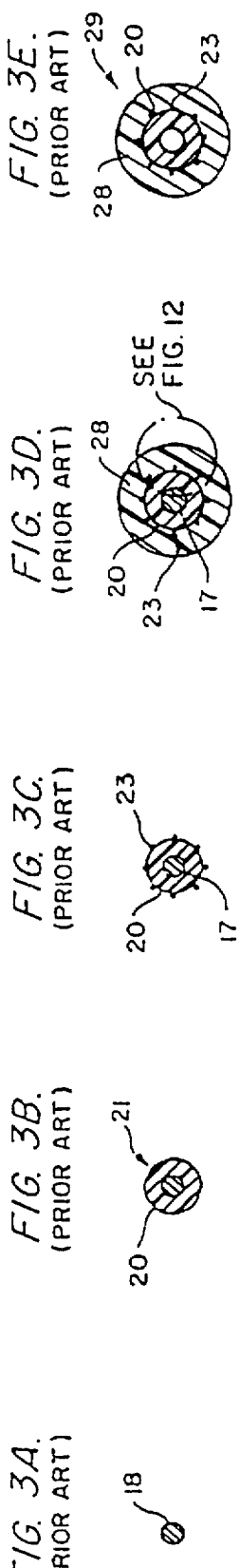

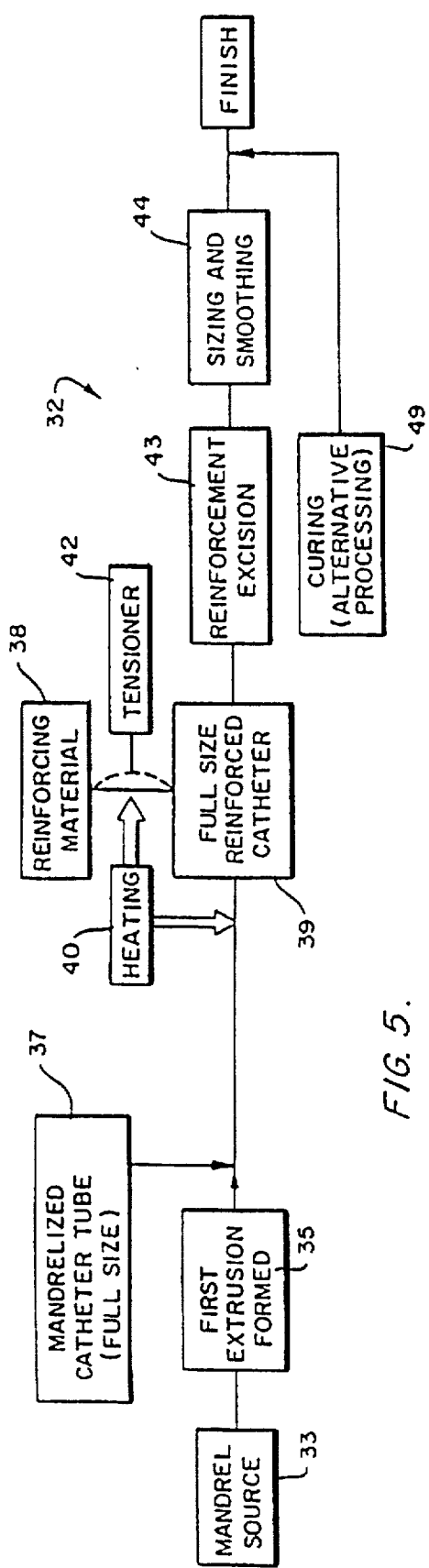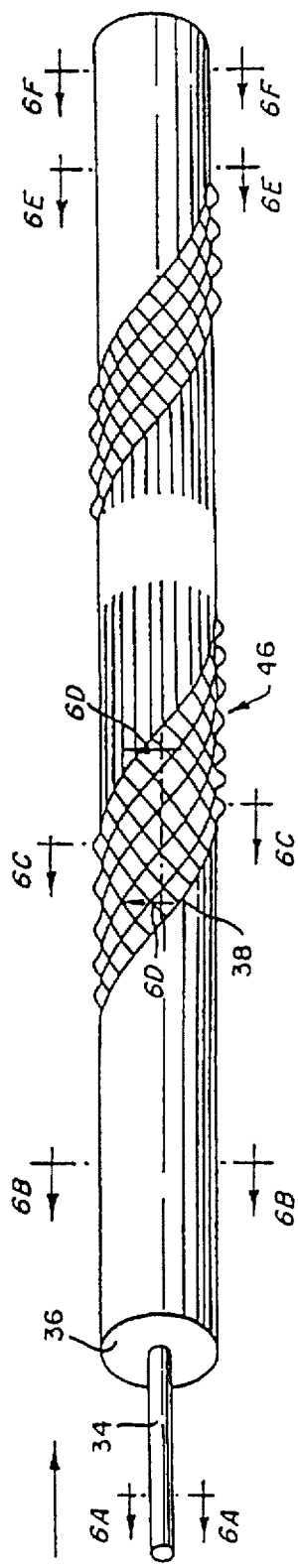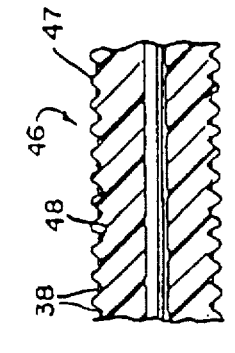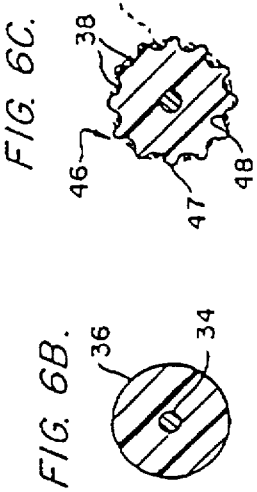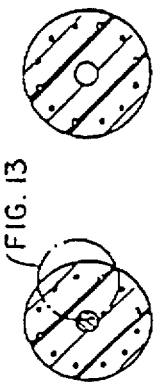

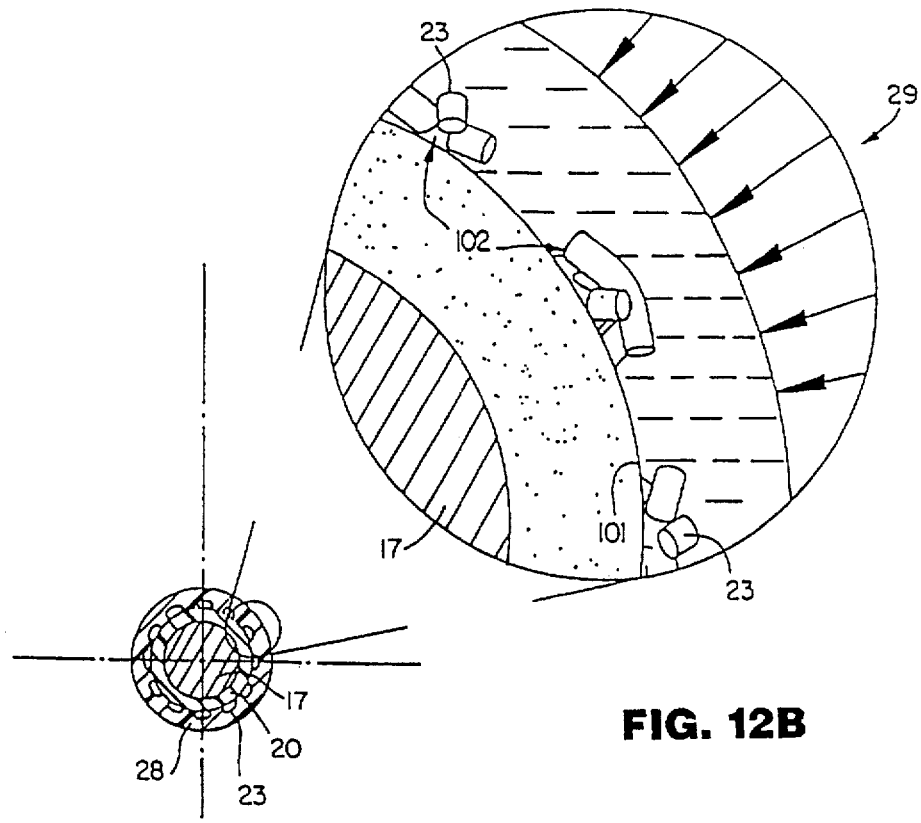
FIG. 12B
FIG. 12A
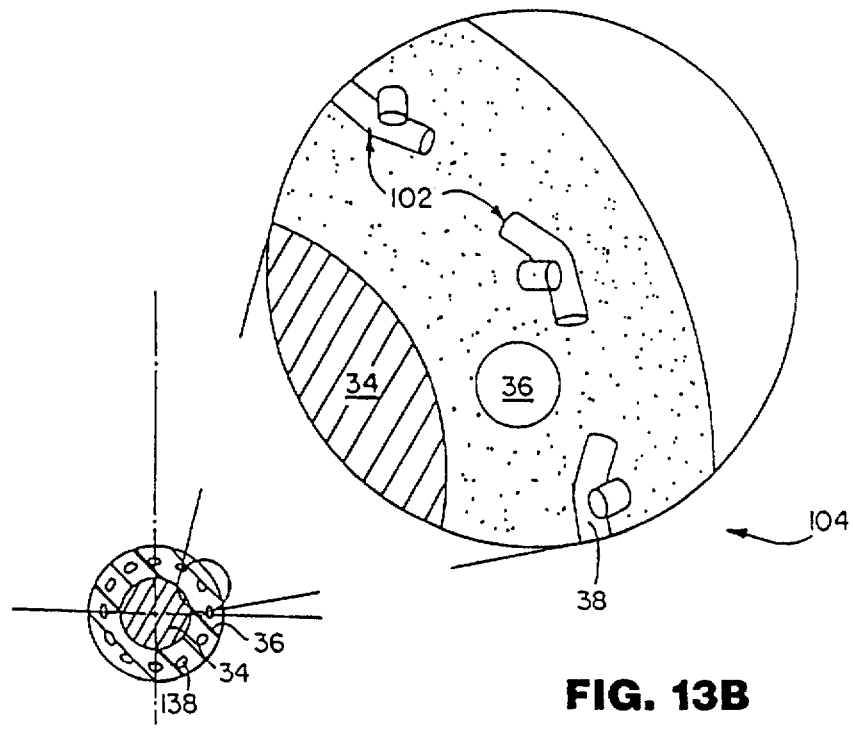
FIG. 13B
FIG. 13A

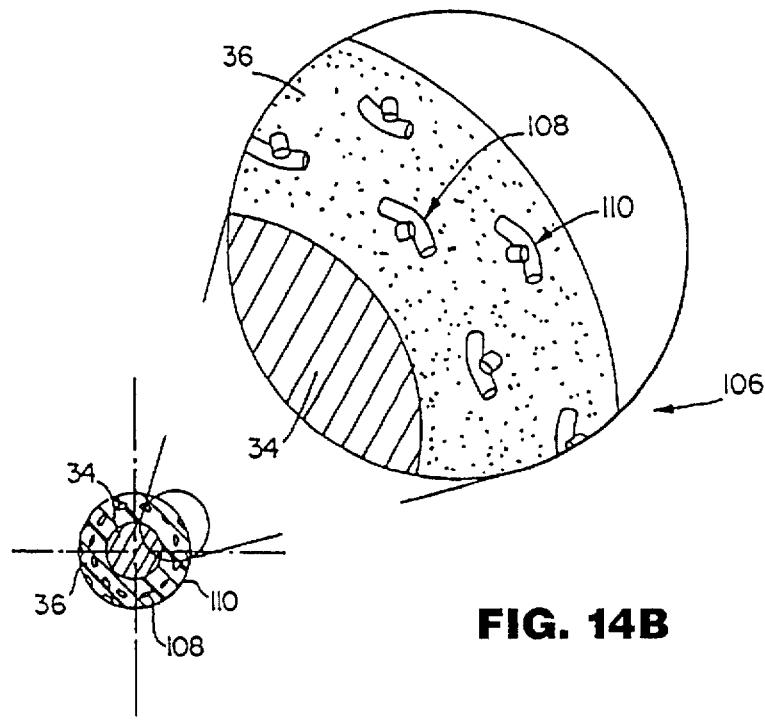
FIG. 14B
FIG. 14A
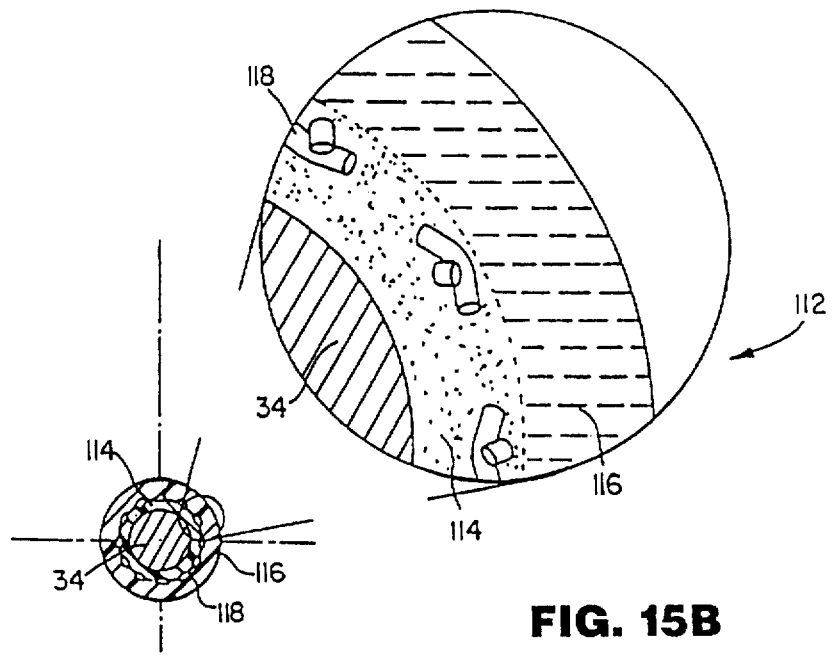
FIG. 15B
FIG. 15A

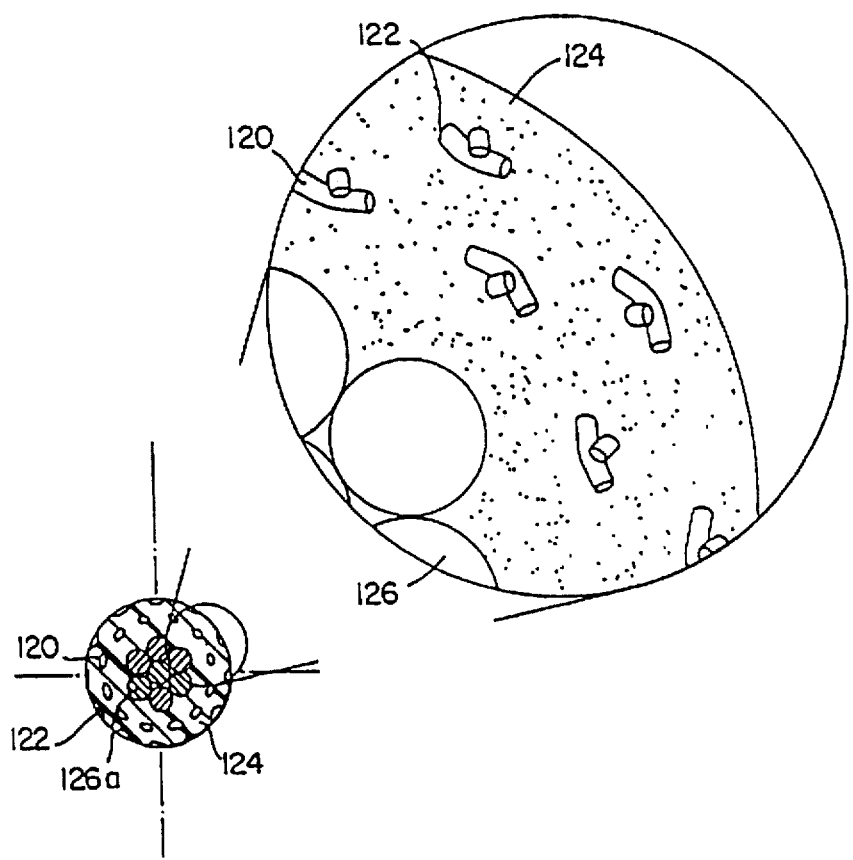
FIG. 16A  FIG. 16B

METHOD FOR MAKING A TUBULAR PRODUCT

This application is a continuation of application Ser. No. 07/474,729 filed Mar. 22, 1990, now abandoned, which is a continuation-in-part of Ser. No. 06/845,492 filed Mar. 31, 1986 now U.S. Pat. No. 4,764,324, which is a continuation application of Ser. No. 06/743,890 filed Jun. 13, 1985, now abandoned, which is a continuation of Ser. No. 06/560,526 filed Dec. 12, 1983, now abandoned.

BACKGROUND OF THE INVENTION

The present invention relates to a method of making tubular products, especially suited for the manufacture of catheters. More particularly, this invention relates to a method for making a reinforced tubular product, such as a reinforced catheter, in a single extrusion step wherein the location of the reinforcement in the wall of the tubular product is simply but accurately controlled. Still more particularly, this invention relates to a method for making a catheter of the type wherein the reinforcement is omitted from the distal end of the catheter through intermittent application of the reinforcement during the manufacturing process. Still more particularly, this invention relates to a method for making a reinforced tubular structure, such as a catheter, wherein the reinforcing material is applied by helically wrapping an intermediate structure with at least a length of reinforcing material and controlling the angle of helical wrapping to control selected physical characteristics of the finished product.

The art of manufacturing tubes, pipes or cannulae by extruding a plastic material to produce significant quantities of the tubing is fairly well developed. In many instances, it is desirable to use reinforcement in the tubes or pipes to increase the pressure, tensile, or torque carrying capacities of those tubes or pipes. Ordinary plastic garden hose reinforced with filament is a common example of such a product made according to prior art techniques.

A special type of tubular product, as is also well known in the art, is a catheter for application in the medical field. Catheters of the type contemplated are relatively thin and flexible tubes which include inner and outer plastic layers with a wire sheathing embedded between the layers. The wire sheathing is either braided or cross-wound to obtain a maximum torsional rigidity and a satisfactory longitudinal flexibility. However, such catheters and in particular those intended for diagnostic purposes, which use radio-opaque dyes and fluoroscopy, to deliver the radio-opaque dyes through the reinforced extruded catheter to the desired site have particular constraints on their construction. Since the dyes are relatively viscous, and the speed of injection is important, high pressures are developed in the relatively small tubing during delivery of the dye. To resist these high pressures, but to retain a degree of flexibility which permits the catheter to be used within a body, it is necessary to reinforce the flexible materials used in the catheter rather than use materials strong enough in their unreinforced state. The latter materials are usually too stiff for use in the vascular system of the human body. Thus, in general, high strength tubes are too stiff for medical use, while highly flexible soft polymers have insufficient strength characteristics so that reinforcement of the softer materials with a higher strength reinforcing material is necessary.

All of the foregoing constraints are measured against the desirability in the art to make the outside diameter of the catheter, including its tip, as small as possible to reach very narrow passages in the body. In that regard, the flexible catheters produced according to the art, in addition to exhibiting satisfactory pressure resistance, must also be able to transmit torque or "twist" from the end remaining outside of the body, i.e., the proximal end, to the other end of the catheter, i.e., the distal end, located inside the body. This torque transmission is required to allow the delivery tip of the catheter to be guided through the twists, turns, valves, and bends in the vascular system of a patient to arrive at the point where dye injection is desired. Such catheters generally have braided metal reinforcement in the wall of the small diameter catheters to withstand pressure of 1000 psi or more.

A typical prior art process for making a reinforced extruded catheter is a three step process. In the first step, a mandrel having an outside diameter equal to the desired inside diameter of the finished catheter is passed through suitable extrusion tooling to cause a tubular jacket or sheath of the catheter material to form around the mandrel. In this step, the outside diameter of the first extrusion layer on the mandrel is smaller than the desired finished outside diameter of the finished catheter. As an alternative, a non-mandrelized tube can be extruded with an ID and OD which are the same as that of the mandrelized tube. Next, the inner core tube formed in the first step as described above is processed by suitable machinery to cause a pattern of reinforcing material, such as wires, fibers, or monofilaments, for example, to be laid along and/or around and in contact with or slightly into the surface of the core tube. Next, the composite intermediate structure of the inner core tube and the reinforcing layer thus applied is again passed through suitable extrusion tooling equipment to deposit a second layer of catheter material around and bonded to the composite thereby encapsulating the non-reinforced inner core tube forming essentially a single structure. The outside diameter of the second layer of extrusion is approximately equal to the desired finished outside diameter of the catheter. Subsequently, finishing and polishing operations can be performed and the composite thus constructed cut to its desired length. The mandrel, if any, is then extracted by lengthwise pulling, leaving the hollow catheter tubing with reinforced walls.

Most catheters require a flexible non-reinforced tubular tip on the end used in the body. Thus, a welding operation is then performed whereby non-reinforced tubing of similar overall dimensions to that of the reinforced body is added to the composite structure, such as by plastic welding. This provides a flexible tip for steering the catheter through the cavities in the body of the patient. It has, however, been a problem in the art that such weldments between the tip and the catheter body are sometimes weak causing the tip to break off during the catheterization procedure.

An advance in the method of manufacture is represented in U.S. Pat. No. 4,321,226 to Marking with regard to the manufacture of a tip wherein wire sheathing is omitted in the tip or distal end. The method there described provides for removing a portion of the wire braid through predetermined lengths of the catheter, such as by cutting, to leave defined, spaced, areas of the catheter without wire reinforcement for subsequent encapsulation by another extrusion. Thus, a unitary catheter, with an end portion without wire reinforcement adjacent to a portion with such wire reinforcement, is produced.

The art of applying braiding or multi-pass wire reinforcement to a catheter inner core is also well developed and machinery for performing such a step is well known. In general, such reinforcement material is applied to the inner core tube in a pattern of right and left-hand helices, each having one or more reinforcements applied over a given area or length of the tube or cannula. However, a typical braiding process causes all reinforcements to be laid down in a direction which passes alternatively over and under all of the reinforcements laid down on the inner core tube in an opposite direction. Thus, the machinery performing the braiding process must move the reinforcements alternately radially inwardly and outwardly, as well as circularly, whereby the tension on the reinforcement continuously varies at a given production speed, and further increases as production speed increases. Such variations, in the extreme, cause the reinforcement to break, especially as the production speed increases. Moreover, the braiding machinery is subjected to significant internal inertial loads, shock loads, and lubrication requirements, especially because of the requirement to generate two directions of movement of the reinforcements at the same time. These shock and inertial loads put a definite upper limit on the speed at the machinery and therefore limit its production rate.

Still another shortcoming of braid-reinforced catheters arises from the oppositely-oriented application of the reinforcing braid resulting in difficulties in transmitting axial torque along the catheter while in use. When such a braided catheter is twisted, one of the helices of the wrap will be tensioned while the other is compressed, resulting in a loss of angular control through the catheter in steering the catheter through the human body, due to inefficiencies in transmitting torque through the elongated catheter body.

Still another difficulty with prior art catheters results from the inherent compromise between stiffness and torque transmission due to the helix angle of the braid. As the helix angle (i.e., the angle of the reinforcement relative to the axis of the catheter) decreases, the apparent stiffness of the catheter increases, but the efficiency of torque transmission decreases. Thus, a tube or catheter with wire parallel to its axis yields the maximum stiffness but the minimum torque transmission efficiency; conversely, a circular wrap has not only the highest torque transmission efficiency but also the poorest stiffness characteristics. Thus, the angle of helical braid generally selected in conjunction with the polymer used is a compromise between these two factors and thus limits the polymers which may be used. It is an aim of the invention to utilize a wrapping technique for applying reinforcement at a high angle (i.e. nearly circular wrap) while also applying a second wrap at a lower angle (more axial) to make integral tip catheters with soft polymers previously unsuitable for use in catheters.

Thus, it is an overall objective of this invention to provide a reinforced catheter of the type described in which the reinforcement materials are provided on an intermittent basis along the body of the catheter and wherein the radial location of the reinforcement layer in the wall of the catheter is precisely controlled, while at the same time reducing the number of steps in the production process.

It is another objective of this invention to provide a method for making a catheter by heating a thermoplastic tube while tensioning the reinforcing member as it is applied to the tube, so that the member deforms or penetrates the softened tube wall to a depth controlled by the degree of tensioning and the plasticity of the tube, whereby, after smoothing and sizing, a single extrusion of a tube at essentially the finished size can produce a reinforced composite tube.

It is another general objective of this invention to provide a method for making a reinforced tube or member by applying a tensioned reinforcing member to an uncured, soft thermosetting resin tube or member so that the reinforcing member penetrates the soft tube or member to a predetermined, controlled depth.

It is another overall objective of this invention to produce a tube by the process described wherein the pattern of the reinforcement is interrupted to provide a straight line of reinforcement at the surface of the tube to permit easy removal of such straight portion when producing, for example, an integral tip catheter.

It is still another objective of this invention to apply a helical wrap to a body of tubular material at a large angle approaching a perpendicular to the axis of the tube and applying a second helical wrap at a small angle approaching the axis of the tub, whereby torque and stiffness of the tube are maximized while expanding the class of polymers which may be used.

It is another general objective of this invention to provide an elongated solid thermoplastic member with a reinforcing material embedded therein to a controlled depth by controlling the temperature of the thermoplastic member and the tension on the reinforcement during manufacture to produce an integral composite.

It is another general objective of the invention to provide a homogeneous monolithic structure with a reinforcing material embedded therein which exhibits an improved tendency to resist separation under pressure at the location of the reinforcement in the wall.

It is another object of this invention to provide a reinforcement of the type described to a coextruded multipolymer matrix wherein the embedment of the reinforcement occurs one or more times.

It is another objective of the invention to provide a plurality of reinforcements by the method according to the invention to a wall of a structure.

It is still another objective of the invention to provide for the embedment of one or more layers of reinforcing material to a thermoplastic sheath having a core of one or more conductors or torque-transmitting members.

These and other objectives of this invention will become apparent from the drawings and the detailed description of the invention.

SUMMARY OF THE INVENTION

The applicant's invention is bottomed on the discovery that by heating the polymer substrate during a process of manufacturing a catheter while simultaneously applying axial tension to the reinforcement structure, the reinforcement material, whether it is a braid, wire, helical wrap, or the like, will be caused to deform or penetrate the original surface of the catheter body polymer and thus to sink into such surface. In practice, it has been found that the distance to which the reinforcement material sinks into the underlying polymer is highly controllable and repeatable depending on the conditions of the relative softness of the catheter body, as well as on the tension exerted on the reinforcing material. For thermoplastic materials, the softness is a function of the temperature of the material while for thermosetting materials, the softness is a function of the uncured polymers. Thus, by controlling these parameters, the radial position of the reinforcement in the wall of the catheter can be simply but accurately controlled.

Following the submersion of the reinforming material into the catheter-polymer body, the polymer thus softened and deformed or penetrated, but remaining outside of the new smaller diameter of the reinforcement structure, produces a somewhat peaked or waffled contour in those locations where the polymer has exuded between the strands or filaments of the reinforcement and extends radially outwardly beyond the reinforcement to an extent where it can be worked to form the outer wall of the catheter body without a second extrusion of the catheter wall as in a prior art process. This second significant feature of the applicant's invention permits a reinforced catheter of the type described to be produced with a single extrusion step followed by a single finishing step, rather than a multi-step extrusion process insofar as the production of the catheter walls is concerned. The peaked, exuded, or waffled contour of the composite reinforcement catheter-polymer construction is then caused to pass through a sized opening in a contour die so that the protrusions of polymer there present are caused to flow in a way to fill the valleys caused by this submersion of the reinforcement material into the polymer wall. Thus, a smooth surface composite construction of polymer containing the embedded reinforcement below the now smooth surface is thus produced. It can thus be seen that a major point of significance in the invention resides in the fact that it eliminates the necessity for multiple extrusions of polymer layers as is now required to build a reinforced polymer composite.

As an alternative, the invention may be produced with a thermosetting material in the form of a tube or solid wherein a reinforcing member under tension is applied to the soft material to embed the reinforcement within the material.

With the composite reinforced catheter body construction produced according to the process described, the reinforcement material may be intermittently applied on and into a single layer of polymer to produce a catheter body in which the distal tip is integral with the catheter body but is devoid of reinforcement to permit the desired flexibility for the tip. In this process, the reinforcement material is applied by submersion through a single layer of polymer extrusion and the pattern of application interrupted into a straight line pattern which is not submerged into the catheter wall body. The straight line, non-submerged, reinforcement structure is then removed so that by using a smoothing die, a non-reinforced section remains, thus forming a unitary catheter tip.

The method according to the invention may be used to produce tubular structures, such as hoses, or composite solid matrixes of thermoplastic material with reinforcement embedded therein. Such composites, whether tubular or solid, exhibit improved resistance to separation at the interface between the material of the composite and the reinforcement. Moreover, one or more reinforcements may be sequentially applied to the base member, whether solid or tubular, to provide a composite structure with a plurality of reinforcing members embedded therein, and those reinforcing members may be the same or different materials to impart desired physical characteristics to the composite. For example, a tubular product may have two reinforcing layers of different materials sequentially and spacedly applied to control the torque transmitting characteristics of the tubular composite, and its apparent stiffness.

The process according to the invention may also be applied to a dual or multipolymer coextended matrix wherein the embedment occurs one or more times to provide an improvement to virtually any current reinforced tubular structure.

The structure provided by the invention is an improvement in the art in that a homogeneous matrix is produced which exhibits improved burst strength. Two-pass prior art techniques where the embedment lies at boundary layer tend to separate at that location and the burst strength is limited to slightly more than that of the first layer and the reinforcement.

Another significant feature of the invention for producing a catheter of the type described resides in the fact that conventional braiding for the reinforcement material may be replaced with helical wrapping as described in detail. The application of reinforcement to tubes with the use of helically wrapped right and left-hand reinforcing materials, sequentially applied instead of woven or braided reinforcing materials, for pressure resistance and torque transmission in tubes or cannulae, is known.

Another feature of the invention resides in the application of a first helical wrapping or braid at a large angle relative to the axis of the underlying tube and a second wrap or braid at a small angle relative to the axis. The application of a multiple set of reinforcements produces tubes or cannulae with precise torque and stiffness thus allowing a broader range of polymers with their broader range of physical properties.

These and other features will become apparent from the description of the drawings and the written description of the invention which follows.

BRIEF DESCRIPTION OF THE DRAWINGS

In the drawings:

FIG. 1 is a block diagram of a prior art process for manufacturing an intermittently reinforced catheter with a unitary reinforced tip;

FIG. 2 is a pictorial diagram, partially in perspective, showing the catheter structure as it progresses through the continuous process diagrammed in FIG. 1;

FIGS. 3A–3E, show cross sections of the composite catheter structure at various steps in the prior art process depicted in FIGS. 1 and 2, a portion of which is shown in greater detail in FIG. 12;

FIG. 4 is a block diagram of the process according to the invention;

FIG. 5 is a pictorial diagram, partially in perspective, showing the structure of the invention at various stages in the continuous process of FIG. 4;

FIGS. 6A–6F, illustrate cross sections of the composite structure at various stages in the process shown in FIGS. 4 and 5 according to the invention, a portion of which is shown in greater detail in FIG. 13;

FIG. 12 is an enlarged view of a portion of the prior art structure shown in FIGS. 3D and 3E;

FIG. 13 is an enlarged view, similar to FIG. 12, of a portion of the structure of the invention shown in FIGS. 6E and 6F;

FIG. 14 is an enlarged view, similar to FIG. 13, illustrating a composite monolithic matrix according to the invention, showing plural layers of reinforcement applied to a solid or mandrelized extruded or coextruded polymer;

FIG. 15 is an enlarged view, similar to FIGS. 13 and 14, illustrating a composite monolithic matrix according to the invention, showing an embedment of a layer or reinforcement in a dual or multipolymer underlying matrix; and FIG. 16 is an enlarged view, similar to FIG. 14, illustrating plural applications of the method according to the invention to produce a structure having plural layers of embedded reinforcing materials and a core at plural strands.

DETAILED DESCRIPTION OF THE PREFERRED EMBODIMENTS

Figure 7:
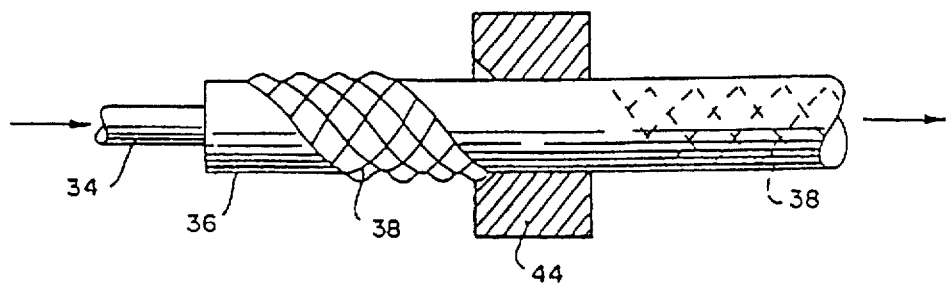
FIG. 7 is a side elevational view, partially in block form, showing the reinforced composite single layer catheter passing through a sizing die to smooth the outer surface to produce a finished catheter.

FIGS. 1–3 describe in greater detail a prior art process for manufacturing a reinforced tube, for example, a catheter, as designated generally by the reference numeral 15. As shown in FIGS. 1–3, a mandrel 17, from a mandrel source 16, comprises an elongated tubular or solid form 17 having a generally circular cross section 18 (FIG. 3A) is passed through a first extruder 19 to provide a sheath 20 of plastic material about the mandrel 17. The mandrel 17 has an outside diameter equal to the desired inside diameter of the finished catheter 15. The innermost layer of the catheter wall is formed from the sheath 20 to form a core tube for the finished catheter and has an inside diameter equal to the outside diameter of the mandrel 17. The plastic sheath 20 about the mandrel 17 during the first extrusion step has an outside diameter which is smaller than the desired finished outside diameter of the finished catheter. As an alternative, a non-mandrelized tube can be extruded with an inside diameter and outside diameter which are the same as that of the thus-mandrelized tube. In such a process, the plastic is usually a thermoplastic material, although other materials such as rubber may be used, and machines for extruding such materials as a sheath are known.

The inner core tube 21 formed as described above is processed by suitable machinery 22, known to the art, to cause a pattern of reinforcing material 23 to be laid along and/or around and in contact with or slightly into the outer surface of the core tube 21. By way of example, the reinforcing material may include wires, fibers, or monofilaments. Where desired, the composite catheter structure with the reinforcing material 23 may be processed to intermittently excise a portion of the reinforcement, as shown generally by step 25. In performing this step, the reinforcement material thus formed is physically removed along spaced portions of the core tube 21, as shown at portion 26 of FIG. 2. Thereafter, the core tube 21 with reinforcement spacedly excised is passed to a second extruder 27 to form a second layer 28 of extruded wall material as a sheath and bonded to the core tube to produce a composite structure having an outer diameter approximately equal to the desired finished outside diameter of the catheter. In performing this step, therefore, the reinforcing layer 23 (whether or not partially excised) is thus embedded in the wall of the final composite catheter structure 28, which wall comprises two radially located sequentially applied extrusion layers bonded together to form a substantially structurally single tube wall. Finally, in the step designated generally by the reference numeral 30, the composite thus constructed is cut to its desired length, and the mandrel 17, if used, is extracted by lengthwise pulling leaving the hollow catheter tubing with intermittent or continuous reinforced walls.

FIG. 12 shows a portion of the structure of FIGS. 3D and 3E in greater detail. By its construction, the prior art requires that the reinforcement layer 23 lie at the boundary of the inner layer 20 and the outer layer 28. However, at that location, the reinforcement layer interferes with the binding of the outer layer 28 when extruded over the inner layer 23 under heat and pressure. Thus, the structure 29 tends to exhibit a tendency to separate along the boundary 101 between the layers 20 and 28 and especially at the cross-over locations 102 of the reinforcement material 23. Moreover, the resultant burst strength is limited to a value only slightly greater than that of the reinforced layer alone since the two layers 20 and 28 tend to fail almost sequentially instead of as one. Even in the areas at the boundary 101 intermediate to the cross-over locations 102, the adhesion or cohesion of the layers is limited because of the radially limited diffusion and intermixing of the layers 20 and 28. Physically, the boundary location 101 may be seen under microscopic examination as a defined layer.

The process for making the tube, such as a reinforced catheter, according to the invention is best seen in its preferred embodiment in FIGS. 4–6. In FIG. 4, the process according to the invention is designated generally the reference numeral 32. As a starting material for the process 32, a mandrel 34 from a mandrel source 33 is passed through an extruder 35 to deposit a sheath 36 about the mandrel 34 in a manner somewhat similar to the first extrusion step of the prior art. However, the outside diameter of the extrusion here is approximately equal to the full outside diameter of the finished catheter. In the alternative, a full size mandrelized catheter tubing may be provided, as representatively shown in block 37, and used as a starting composite for further processing according to the invention wherein the catheter tubing has an outside diameter approximately equal to the final outside diameter of the finished catheter.

Reinforcing material 38 is applied to the mandrel/tubing composite structure 39 in a manner similar to that described in connection with FIG. 1.

However, it has been found that the application of heat by a suitable heat source 40 to the mandrelized wall tubing acting as a starting material while simultaneously tensioning the reinforcing material by a tensioning device 42, will cause the reinforcing material when applied to the original surface of the catheter body to sink into such surface and to penetrate or deform it. The heat thus applied to a thermoplastic material forming the catheter body causes the thermoplastic polymer to soften to an extent sufficient to permit such penetration or deformation.

It has been found that the distance into which the reinforcement material penetrates beneath the surface of the catheter body and thus sinks into the underlying polymer is highly controllable and repeatable. That distance is a function of the relative temperatures of the catheter body and the reinforcement material, as well as the simultaneous tension exerted on the reinforcing material by the tensioning device. Thus, by way of example, if the temperature applied to the catheter body is controlled within toleranced limits, for a given catheter body made from a known polymer exhibiting known viscosity as a function of temperature, the depth of penetration of the reinforcing material can be determined for a given process rate and time of application virtually solely by the degree of tensioning applied by the tensioning device.

In an alternative practice of the invention, assuming that the tensioning is fixed within toleranced limits, the degree of heating of the catheter body and the reinforcement material, but preferably only the catheter body, will similarly control the depth of penetration at a constant process speed. In its simplest form, controlling the temperature of the heat source 40 will control the degree of heating of the catheter body composite at that stage in the process. Since the process is practiced on a continuous basis, the heating temperature may also be controlled by the speed of the process, by way of example, by passing the mandrelized catheter body through a heat source 40 providing a source of heat within toleranced limits. A representative way of applying heat to the catheter body 36 is by passing the catheter body 36 through an oven, or through a fluid heat transfer medium for a time sufficient to permit the catheter body 36, or at least the radially-outwardly extending portion of the catheter body 36, to soften to an extent which permits it to receive the reinforcing material 38 therewithin.

Such a process has significant advantages in controlling the placement of the reinforcement material 38 in the wall of the catheter body and thus is particularly suited for applications in which it is necessary to structure a catheter such that the reinforcing material 38 is located near the outer wall of the catheter, near the inner wall of the catheter, or at a precisely-controlled selected point in between. When it is remembered that catheter bodies are extremely small structures and catheter walls are extremely thin, such a process has significant advantages in assuring that the reinforced materials are embedded within the catheter wall throughout the length of the catheter while at the same time omitting the second extrusion step as previously discussed in connection with FIG. 1.

FIG. 5 and FIGS. 6A–6F further illustrate the features of this aspect of the invention. Following the submersion of the reinforcing material 38 into the catheter body made from a thermoplastic polymer, the polymer thus softened and penetrated, but remaining outside the new smaller diameter of the reinforcement structure, produces a peaked or waffled contour, designated generally by the reference numeral 46 (FIG. 6C) in those locations where the polymer has exuded between the penetrating stands of the reinforcing material 38. Thus, in FIG. 6C, the outside diameter of the composite catheter prior to application of the reinforcing material is designated by a dotted line by the reference numeral 47 to illustrate that in general the peaked areas 46 extend beyond the former outside diameter of the catheter body, while the valley areas formed near the reinforcement material (designated generally by the reference numeral 48) generally inwardly peak at the location of the reinforcing material 38 at a radially outwardly extending distance less than that of the former outside diameter 47 of the catheter body. Such a formed structure is advantageous in that in subsequent processing, the protruding portions 46 may be smoothed over in a sizing and/or smoothing step 44 to form a smooth catheter wall completely enveloping and embedding the reinforcement material 38 as seen in FIGS. 6E and 6F. More significantly, such a step avoids the application of a second extrusion.

Returning to FIG. 4, the composite structure with the waffled contour as shown in FIG. 6C, if desired, may be processed to intermittently excise a portion of the reinforcement 38 to form a unitary catheter or alternatively, where intermittent reinforcement is not desired, to pass directly to a sizing die for smoothing the outer wall to make the final product. In the sizing die, the protrusions 46 are caused to flow in such a way as to fill the valleys 48 caused by the submersion of the reinforcement material 38 into the polymer wall 36. Thus, a smooth surface composite construction of a polymer containing the embedded reinforcement material 38 below the now smooth surface 49 is thus produced. Thus, the sizing and smoothing step 44 in the process is shown in greater detail in FIG. 7.

In the process according to the invention, the composite reinforced catheter body construction produced according to the invention may have the reinforcement material continuously applied, as in the prior art, and subsequently excising portions thereof, or continuously applying the reinforcement but in such a way as to cause the reinforcement material to lie along the outer surface of the composite structure as a series of straight line strands as shown in FIG. 5 and in FIGS. 8–10 as will be explained in greater detail. Such a straight line pattern is not submerged into the catheter wall body and thus easily removed from the surface of the composite structure so that upon smoothing in a smoothing die, a non-reinforced section remains, thus forming a unitary catheter tip.

The process of the invention may be performed continuously utilizing conventional machinery. Thermoplastic polymer mandrels, extruders, and machines for applying reinforcing material, such as braiders, are known to the art. For example, braiding machines are available from either New England Butt Company or Wardwell Company.

As specific examples of the type of thermoplastic materials which may be used, such materials include polyethylene, polyurethane, certain rubbers, latexes, and vinyls, conventionally available from such companies as DuPont. Presently, for catheter construction, urethane thermoplastic materials are preferred. As a specific example of a preferred reinforcement material, one may use polyaramid, which is commercially available under the trademark "KEVLAR", but other materials such as carbon boron fiber, glass, ceramic, non-metallic wires, metallic wires (DBS), and natural fibers such as cotton, as well as monofilaments such as nylon and polyester, may also be used. Where it is desired to utilize the reinforcement material as a conductor for signals, an electrically conductive wire may be used as all or any part of the reinforcement material.

FIG. 13 shows a portion of the structure of FIGS. 6E and 6F in greater detail. Such a structure 104 is characterized as having a monolithic, integrated wall 36 uninterrupted by a boundary such as the boundary 101 as seen in FIG. 12. The resultant burst strength is that of the composite monolithic, unitary, reinforced structure which must burst as a unit rather than as sequentially thinner layers as in FIG. 12. The invention may thus be used to produce catheters as small as 3 Fr (about 0.039") up to 45 Fr (about 0.5895") with accurate reinforcement embedment.

The embodiment of FIG. 4 has been described with respect to thermoplastic polymers forming the catheter body, using heat as the medium for controlling the plasticity of the wall to permit penetration of or deformation by the reinforcing material to form the waffled contour 46. In the alternative, as shown by the step bearing the reference numeral 49, other curable polymers may also be used. Where, for example, the polymer may be hardened by curing by cross-linking under the application of ultra-violet light, or by ionizing radiation, a curing step particular to the curable resin may be used. Such curable polymers may possess a sufficiently semi-rigid body characteristic prior to curing to permit penetration into, or deformation of the surface by the application of the reinforcement material, as previously described, or to form the waffled contour without the application of heat as described in connection with FIG. 4. In those instances, the step of applying heat may be eliminated in favor of a curing step after the application of the reinforcement material and its partial excision as described and during or after sizing as shown in step 44. These alternative times of application of the curing step subsequent to the application of the reinforcement material to the catheter body being formed are designated generally by the two arrows connecting the block 49 to the process of FIG. 4. However, depending on the characteristics of the material used, a curing or partial curing step may be carried out either earlier or later in the process while carrying out the essential features of the invention.

Again depending on the material used, it also may be desirable to use a combination of the heating step 40 to soften the body of a curable material, followed by the excision, sizing, and smoothing, and by curing steps to cure and harden the polymer, such as by ultra-violet light, radiation or the application of a curing agent to the material to harden its structure to a condition suitable to its end use.

Another significant feature of the invention relates to the intermittent reinforcement for tubes or cannulae wherein the reinforcement is not continuous, while the tube or cannula is continuous yielding a tube or cannula with reinforced and non-reinforced area sequentially spaced in any desired combination of spaced reinforced and non-reinforced sections along the tube.

Figure 8:
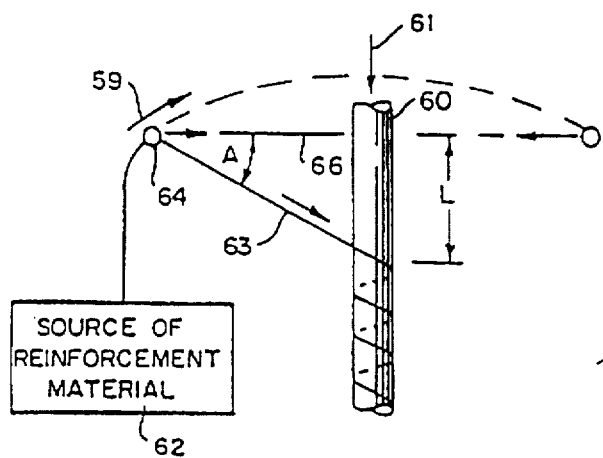
FIG. 8 illustrates in diagrammatical form the step of helically wrapping reinforcement material about a tube.
Figure 9:
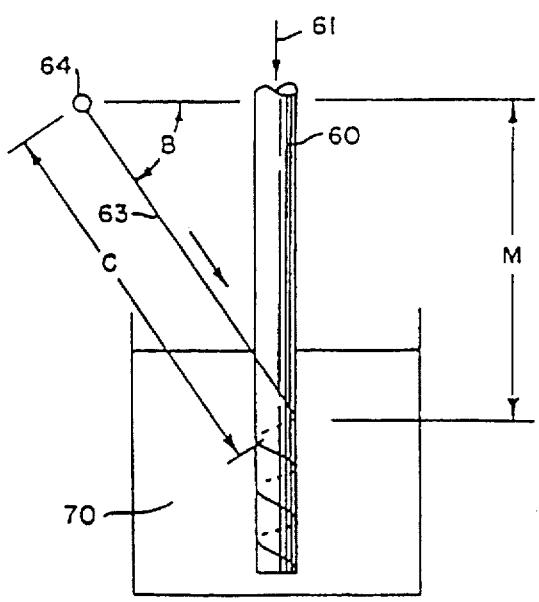
FIG. 9 is a view similar to FIG. 8 illustrating the intermittent helical wrapping of the composite character structure to permit excision of intermittently spaced portions of the reinforced portions of the reinforcement remaining on the surface of the tube to produce a unitary catheter.
Figure 10:
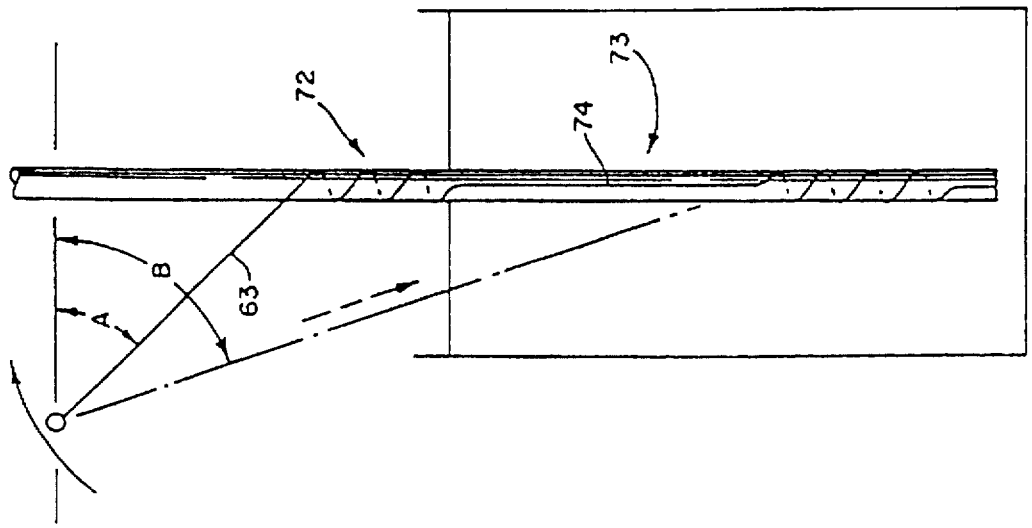
FIG. 10 is a view similar to FIGS. 8 and 9 showing the laying of material on or near the surface of the tube or cannula and adjacent to embedded reinforced sections of the catheter.

As thus seen in FIGS. 8–10, a tube or cannula 60 moving in the direction designated generally by the arrow 61 in the process of FIG. 4 is reinforced by the helical application of reinforcement material 63 passing through a rotating guide 64 from a source of reinforcement material 62. As the guide 64 rotates around tube or cannula, as designated generally by the arrow 59, while guiding the reinforcement material 63 to be wrapped about the tube 60 which is advancing in the direction of the arrow 61, the reinforcement assumes an angle A which is also the helix angle of the reinforcement in the tube 60. The angle A is the result of the ratio between the number at turns around the tube to the distance the tube advances during those turns. This results in a length L between the plane of rotation of the guide 64, defined by the path of the arrow 59, designated generally by the reference numeral 66 as the tube advances in the continuous process.

As shown in FIG. 9, if the guide 64 carrying the reinforcement 63 stops rotating about the tube 60, but the tube 60 continues advancing in the direction of the arrow 61, the reinforcement 63 assumes an angle B which constantly increases as the tube advances thus approaching, but never reaching a true parallel condition with the axis of the tube 60. Under these conditions, a length M of the tube which is not wrapped with reinforcement is caused to form and the length M will continue to increase while the rotation of the reinforcing guide 64 is stopped. If a cooling medium, for thermoplastic resins, or a curing material for a curable resin, or for thermosetting or other curable polymers, is provided at the location defined by the length M, the advancing tube or cannula 60 carries the last area of wrapped reinforcement into a environmental structure 70 causing solidification of the tube prohibiting further embedding of the reinforcement therein. In addition, as the angle B increases, the four force vectors of the tension on the reinforcement reduce the pressure to cause embedment according to the relationship F=T B. Thus, after the desired length M is developed, to define the wrapped length followed by the unwrapped length, wrapping or braiding resumes (as in FIG. 10), causing the resumption of the angle A defining the length L which is outside of the area of cooling or curing, thus allowing resumption of the embedding process in the soft or uncured polymer. In addition, the last end of the straight unembedded reinforcement is captured when embedding restarts.

As best seen in FIG. 10, as a result of the starting and stopping of the wrapping braiding operation, the reinforced tube or cannula 60 thus generated has areas 72 of helically wrapped or braided embedded reinforcement 63 sequentially followed by lengths 73 of tube or cannula in which the wrap or braid is not embedded within the wall of the structure but rather is laying on or near a surface of the tube or cannula, as designated generally by the reference numeral 74. Therefore, as a subsequent operation to the reinforcement application, the straight loose reinforcement thus positioned can be cut away or removed so that upon final finishing, as described in connection with FIG. 4, that portion of the tube or cannula is unreinforced while the remainder of the tube or cannula is reinforced.

An advantage in using the helical wrapping process of the type described in connection with FIGS. 8–10, in addition to its convenience for removing the reinforcement, is that the machinery to perform such an operation only rotates the reinforcement in smooth circles, as understood from the plane 66 generated by the path 59 of rotation shown in FIG. 8. Thus, no tension changes in the reinforcement or inertial shockloads in the machinery result. Thus, the only significant practical limits on the speed of production are the structural loads of the centrifugal force on the bearings and components, thus resulting in a speed increase over braiding or a factor of four or more. In addition, a catheter utilizing such a process avoids the problems described in efficiently transmitting the torque through the catheter during the use procedure. As can be seen, the transmitted torque takes the form of tension in the appropriate reinforcement. The tensile torque thus acts in a straight line parallel to the axis of the reinforcement material since the reinforcement material is supported by the substrate. In the braided structure, as in FIG. 1, for example, where the reinforcement is in a zigzag pattern caused by its alternate passage over and under other reinforcements, the tension force in the reinforcement first tries to straighten the reinforcement back into a straight line before transmitting the remaining torque. This operation is somewhat similar to the step of "taking up slack" required by a plurality of zigzag patterns in a sample length of braided reinforcement and thus causes a sponginess or need to overtwist the structure to cause the distal end to rotate in the desired amount.

On the other hand, according to this process of helically wrapping the reinforcement structure, the tension forces causes by twisting are transmitted axially down the reinforcements by the shortest possible path increasing the efficiency of torque transmission through the catheter structure. Such torque losses as exist are thus caused primarily by substrate deflection and are common to both braided and wrapped structures. Accordingly, torque transmission efficiency through the thus-wrapped catheter is improved significantly.

Figure 11:
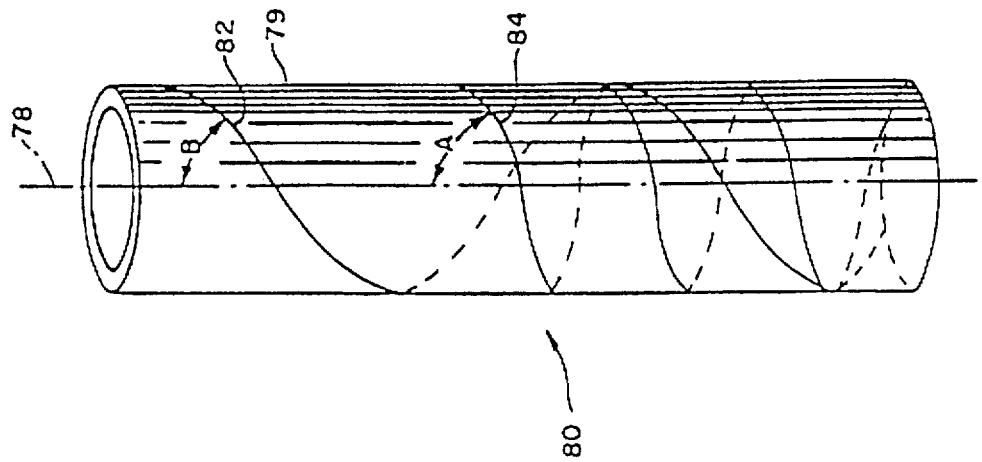
FIG. 11 is a diagrammatical view of a multiply-wrapped catheter according to the invention.

FIG. 11 shows still another aspect of the process according to the invention which utilizes a plurality of wrapped reinforcement structures, designated generally by the reference numeral 80. By using the wrapping technique of applying reinforcement, it is possible to apply reinforcement 82 at a low angle B to the axis 78 approaching circular patterns parallel to the axis 78 of the tube 79, while also simultaneously or sequentially applying another set of reinforcements 84 at a high angle, i.e. at an angle more closely normal to the axis 78. The double set of reinforcement helices from the plurality 80 thus produced allows the design of tubes or cannulae with precise torque or stiffness characteristics, while also using a broader range of polymers than heretofore have been available. This step allows the making of integral tip catheters with tip portions which are softer than those known to the art since there is less consideration given to the polymer stiffness in making the body of "shank" of the catheter. Thus, in FIG. 11, the reinforcement material 84 is applied at an angle A responding to the torque and pressure reinforcement requirements of the catheter, while a second reinforcing helix is applied at an angle B. The numbers and angles of both type of reinforcements with respect to the axis are variable with respect to each other and with respect to the axis of the tube or cannula, resulting in a significant flexibility in tuning the desired characteristics of the catheter to those which produce the features sought.

Thus, an improved method of making a reinforced tube or catheter is described.

The foregoing discussion has concentrated on the application of the invention to the making of a catheter starting with a mandrelized structure. It is clear, however, that the invention may be used to produce other larger size tubular structures, such as radiator hoses, garden hoses, electrical conductors, torque transmitting devices, and the like where the tubular wall structure housing a core material is reinforced according to the invention.

As seen in FIG. 14, a composite monolithic matrix 106 having a plurality of layers 108, 110 embedded therein may be made according to the invention. As one example, a composite made according to the process previously described in accordance with FIGS. 4–6 is again subjected to a heating step, followed by the application of another layer of reinforcing material. Thus, two or more layers of reinforcing materials may be embedded in the wall of the monolithic matrix 106 without the intermediate extrusion steps required by the prior art, while obtaining the invention. The reinforcement layer 108 is first embedded at a location radially closest to the core, followed by a layer 110 at a location radially outwardly from the layer 110. More than two such layers may be embedded where the wall thickness is appropriate to receive plural layers.

FIG. 15 illustrates the application of the invention of FIGS. 4–6 to a multipolymer underlying matrix. It is known in the art to coextrude a single matrix of more than one polymer for particular applications. The invention as described is equally applicable to such multipolymer matrices. Moreover, more than one layer of embedded reinforcement may be applied, as in FIG. 14, to such a coextruded matrix by using multiple passes to apply multiple layers of embedded reinforcement. Thus, in FIG. 15, a matrix 112 is formed by coextrusion of two representative polymers 114, 116 as is known in the art, and the reinforcing layer 118 provided in accordance with the previous discussion.

FIG. 16 shows a representative example of the application of plural layers of reinforcing layers 120, 122 to the full wall of a composite, monolithic matrix 124, housing a plurality of centrally-located members 126, such as conductors, or cable, in the form of a seven-strand core 126a. The material is extruded, as is known in the art, on stranded wire machinery. Plural reinforcing layers 120, 122 are supplied to the matrix 124 to create, for example, a high compression, high torque, flexible drive shaft, utilizing the teachings of the invention.

I claim:

1. A method of making a reinforced finished product with a single extrusion step, said finished product having an accurate outer dimension, comprising the steps of:

providing as an interim structure an extruded structure of a thermoplastic material having an outer dimension about equal to the outer dimension of the finished product;

providing said interim structure in a state heated to an extent which permits a reinforcing member under tension to be submerged to a controlled depth completely beneath the surface of the heated thermoplastic structure;

applying said reinforcing member at the surface of said heated interim structure under sufficient tension to cause said reinforcing member to travel inwardly through the surface of said heated interim structure to cause the surface to become irregular relative to the reinforcing member and to an extent which locates said reinforcing member completely within the product at a controlled location beneath the surface of the interim structure, thus defining a construction composite having surface portions which lie outwardly and inwardly of the former dimension of the interim structure, the volume of displaced material of said interim structure being at least equal to the volume of said reinforcing material added to said interim structure, as least a combination of temperature and material of said interim structure, and tension on said reinforcing member controlling said controlled location, and smoothing said irregular surface to form said finished product with the reinforcement member located within said finished product, the process being carried out without extruding another thermoplastic layer thereon to achieve the final desired outside diameter, wherein the step of applying a reinforcing member further comprises the step of applying a length of reinforcing material at a preselected helix angle to said structure relative to its axis, and wherein the step of applying said reinforcing member at a preselected helix angle further comprises the step of rotating a guide carrying said reinforcing member in a path approximately normal to the axis of said structure, the helix angle being defined by the length of movement of the structure for each rotation of said guide, and further comprising the step of ceasing rotation of said guide to decrease said helix angle relative to an axis of said structure to define a length of structure in which said reinforcing member lies along the surface thereof during the time the guide has ceased rotating, whereby excision of said reinforcing member from the surface of said structure may be carried out to excise spaced portions of said reinforcing material from aid tubular structure.

2. The method of claim 1 wherein the step of applying includes the step of tensioning the reinforcement member while being applied to said heated structure to cause said reinforcement member to deform the surface of said heated product to form said irregular outer surface.

3. The method of claim 2 wherein the step of tensioning includes the step of controlling the tension on said reinforcing member while being applied to said interim heated structure thus to control the depth of penetration of the reinforcing member into the surface of said structure toward an axis thereof, thereby to control the location of said reinforcing member in the wall of said product.

4. The method as set forth in claim 1 further including the step of intermittently excising a selected length of said reinforcement member form said structure to form a product having spaced reinforced and non-reinforced lengths.

5. The method as set forth in claim 1 wherein the step of applying includes the step of heating said interim thermoplastic structure sufficient to permit the reinforcing member to cause the outer surface of said structure to become irregular when the reinforcing material is applied therein.

6. The method as set forth in claim 5 wherein the step of heating includes the step of heating both the thermosetting interim structure and the reinforcement member while being applied to the interim structure.

7. The method as set forth in claim 1 wherein said structure is made from a curable material, said method including the step of curing said structure after the application of said reinforcing member thereto.

8. The method as set forth in claim 7 wherein the step of curing is carried out immediately following the step of smoothing.

9. The method as set forth in claim 7 further including the step of periodically excising a selected length of said reinforcement member from said structure having spaced reinforced and non-reinforced lengths, the step of curing being carried out after the step of excising.

10. The method of claim 1 wherein the step of applying includes a step of applying as said reinforcing member a braid comprising a plurality of reinforcing members applied to said heated structure in a spaced array.

11. The method as set forth in claim 1 wherein the step of applying a reinforcing member includes the step of applying a first helically wrapped array to the outer surface to the structure at an angle relative to the axis of said structure, and applying a second helically wrapped array at another angle relative to said axis, whereby the torque transmission efficiency and apparent stiffness of the product may be controlled.

12. The method as set forth in claim 1 wherein the step of providing includes providing a mandrelized tube structure and includes the step of providing a mandrel, and the step of extruding a tubular structure as a sheath about said mandrel, said tubular structure having an outer diameter approximately equal to the outer diameter of the tubular product.

13. The method as set forth in claim 1 wherein said product is a catheter.

14. The method as set forth in claim 1 wherein said applying step is repeated to provide a plurality of layers or reinforcing members in said structure.

15. The method as set forth in claim 1 wherein said structure is a coextruded structure.

* * * * *